United States Patent [19]

Hildebrand et al.

[11] Patent Number: 5,861,431
[45] Date of Patent: *Jan. 19, 1999

[54] INCONTINENCE TREATMENT

[75] Inventors: Keith R. Hildebrand, Houlton, Wis.; Jan Ellen O. Fowler, St. Paul; Dezso K. Levius, Bloomington, both of Minn.

[73] Assignee: Iotek, Inc., Minneapolis, Minn.

[*] Notice: This patent issued on a continued prosecution application filed under 37 CFR 1.53(d), and is subject to the twenty year patent term provisions of 35 U.S.C. 154(a)(2).

[21] Appl. No.: 477,474

[22] Filed: Jun. 7, 1995

[51] Int. Cl.$^6$ .................................................. A61K 31/19
[52] U.S. Cl. .......................... 514/557; 514/558; 514/559; 514/560; 514/561; 514/562; 514/563; 514/564; 514/565; 514/566; 514/567; 514/568; 514/569; 514/570; 514/571; 514/572; 514/573; 514/574
[58] Field of Search ..................................... 514/552, 558, 514/559, 560, 561, 562, 563, 564, 565, 566, 567, 568, 569, 570, 571, 572, 573, 574

[56] References Cited

U.S. PATENT DOCUMENTS

| | | | |
|---|---|---|---|
| 1,652,327 | 12/1927 | Richter . | |
| 1,776,357 | 9/1930 | Hart . | |
| 1,819,368 | 8/1931 | Hart . | |
| 2,499,045 | 2/1950 | Walker et al. | 128/261 |
| 2,584,166 | 2/1952 | Stevenson et al. | 167/64 |
| 3,076,829 | 2/1963 | Reimann et al. | 260/397.45 |
| 3,347,880 | 10/1967 | Robinson | 260/397.5 |
| 3,392,165 | 7/1968 | Edwards et al. | 260/239.55 |
| 3,519,677 | 7/1970 | Jeger et al. | 260/479 |
| 3,608,075 | 9/1971 | Glen et al. | 424/238 |
| 3,881,026 | 4/1975 | Shepherd et al. | 426/223 |
| 3,920,634 | 11/1975 | Dinner | 260/239.55 R |
| 3,941,131 | 3/1976 | Ogle | 128/237 |
| 4,011,314 | 3/1977 | Petzoldt et al. | 424/241 |
| 4,029,779 | 6/1977 | Petzoldt et al. | 424/243 |
| 4,076,811 | 2/1978 | Lachnit-Fixson et al. | 424/239 |
| 4,082,780 | 4/1978 | Miki et al. | 260/397.5 |
| 4,096,254 | 6/1978 | Benson et al. | 424/242 |
| 4,098,899 | 7/1978 | Schwartz | 424/300 |
| 4,154,820 | 5/1979 | Simoons | 424/175 |
| 4,291,014 | 9/1981 | Keith et al. | 424/28 |
| 4,291,028 | 9/1981 | Vorys | 424/238 |
| 4,315,925 | 2/1982 | Hussain et al. | 424/239 |
| 4,321,252 | 3/1982 | Keith et al. | 424/28 |
| 4,346,709 | 8/1982 | Schmitt | 128/260 |
| 4,364,392 | 12/1982 | Strother et al. | 128/325 |
| 4,372,951 | 2/1983 | Vorys | 424/239 |
| 4,383,993 | 5/1983 | Hussain et al. | 424/239 |
| 4,402,695 | 9/1983 | Wong | 604/892 |
| 4,425,339 | 1/1984 | Pitchford | 424/239 |
| 4,478,822 | 10/1984 | Haslam et al. | 424/78 |
| 4,557,934 | 12/1985 | Cooper | 424/128 |
| 4,562,196 | 12/1985 | Horn et al. | 514/332 |
| 4,585,652 | 4/1986 | Miller et al. | 424/83 |
| 4,605,649 | 8/1986 | Liehr | 514/182 |
| 4,606,337 | 8/1986 | Zimmermann et al. | 128/156 |
| 4,629,449 | 12/1986 | Wong | 604/55 |
| 4,640,912 | 2/1987 | Hausman | 514/54 |
| 4,681,875 | 7/1987 | Laurent et al. | 514/182 |
| 4,729,999 | 3/1988 | Young | 514/227 |
| 4,738,957 | 4/1988 | Laurent et al. | 514/182 |
| 4,746,508 | 5/1988 | Carey et al. | 424/88 |
| 4,788,062 | 11/1988 | Gale et al. | 424/449 |
| 4,788,063 | 11/1988 | Fisher et al. | 424/449 |

(List continued on next page.)

FOREIGN PATENT DOCUMENTS

| | | |
|---|---|---|
| 0 438 078 A2 | 7/1991 | European Pat. Off. . |
| 0 357 581 B1 | 7/1993 | European Pat. Off. . |
| 91 16021 | 10/1991 | WIPO . |
| WO 92/03141 | 3/1992 | WIPO . |
| WO 93/00894 | 1/1993 | WIPO . |

OTHER PUBLICATIONS

Chemical Abstracts AN 1995:238641, Schmidt et al. Jan. 1994.
"Doctor's Guide to Medical and Other News", Jan. 1993.
Urology, vol. 32, No. 3, 1988, pp. 273–280, XP000601200.
Obstet. Gynecol. Clin. North. Am., vol. 21, No. 2, 1994, pp. 357–379, XP000602330.
Gynecol. Obstet. Invest., vol. 29, 1990, pp. 211–213, XP000601195.
Zentralbl. Gynakol., vol. 108, No. 14, 1986, pp. 851–856, XP000601214.
Chemical Abtracts, AN 1996:122326, Bachman., 1995.
Chemical Abstracts, AN 1996:46950, Makinen et al., 1995.
Chemical Abstracts, AN 1983:400678, Batra et al., 1983.
Chemical Abstracts, AN 1983:417521, Lindskog et al., 1982.
Alastair G. S. Tulloch and Alain B. Rossier, "Intraurethral Pressure Response to the Mucosal Application of Neuropharmacologic Agent," 31 *Urol int.* 165–70 (1976).
Arne Nergardh, "The Functional Role of Adrenergic Receptors in the Outlet Region Of The Urinary Bladder," 8 *Scand. J. Urol. Nephros.* 100–07 (1974).
Rosenzweig et al., "Location and Concentration of Estrogen, Progesterone, and Androgen Receptors in the Bladder and Urethra of the Rabbit," 14 *Neurology and Urodynamics* 87–96 (1995).
Wall et al., *Practical Urogynecology* 140–43 (1993).
Elia et al., "Estrogen Effects on the Urethra: Beneficial Effects in Women With Genuine Stress Incontinence," 48 *Obstetrical and Gynecological Survey* 509–17 (1993).
Smith's *General Urology* 7–11 (14th ed. 1995).
Wall et al., *Practical Urogynecology* 8–24 (1993).
Weimar et al., "5–Fluorouracil Urethral Suppositories for the Eradication of Condyloma Acuminata," 120 *J. of Urology* 174–75 (Aug. 1978).

*Primary Examiner*—Keith D. MacMillan
*Attorney, Agent, or Firm*—Merchant, Gould, Smith, Edell, Welter & Schmidt, P.A.

[57] ABSTRACT

The present invention provides a method of treating incontinence in a patient that has a bladder and a urethra. The urethra forms a lumen for draining the bladder. The method comprises the steps of delivering an agent into the lumen and passing the agent from the lumen to internal body tissue. The agent increases restriction of the lumen thereby providing increased control over urine flow from the bladder.

23 Claims, 2 Drawing Sheets

OTHER PUBLICATIONS

| | | | |
|---|---|---|---|
| 4,804,541 | 2/1989 | Nichols | 424/449 |
| 4,826,831 | 5/1989 | Plunkett et al. | 514/170 |
| 4,835,174 | 5/1989 | Roberts | 514/178 |
| 4,849,220 | 7/1989 | Nielsen et al. | 424/659 |
| 4,871,543 | 10/1989 | Lindskog et al. | 424/432 |
| 4,883,669 | 11/1989 | Chien et al. | 424/448 |
| 4,894,373 | 1/1990 | Young | 514/239.2 |
| 4,911,707 | 3/1990 | Heiber et al. | 424/449 |
| 4,917,676 | 4/1990 | Heiber et al. | 424/449 |
| 4,925,673 | 5/1990 | Steiner et al. | 424/455 |
| 4,948,593 | 8/1990 | Wright et al. | 424/473 |
| 4,977,147 | 12/1990 | Jungblut et al. | 514/171 |
| 5,010,056 | 4/1991 | Boghen et al. | 514/12 |
| 5,023,084 | 6/1991 | Chieni et al. | 424/448 |
| 5,024,998 | 6/1991 | Bodor | 514/58 |
| 5,068,226 | 11/1991 | Weinshenker et al. | 514/58 |
| 5,089,482 | 2/1992 | Hermens et al. | 514/58 |
| 5,135,480 | 8/1992 | Bannon et al. | 604/20 |
| 5,145,682 | 9/1992 | Chien et al. | 424/448 |
| 5,183,814 | 2/1993 | Dukes | 514/171 |
| 5,188,835 | 2/1993 | Lindskog et al. | 424/432 |
| 5,189,212 | 2/1993 | Ruenitz | 562/468 |
| 5,198,223 | 3/1993 | Gale et al. | 424/449 |
| 5,204,339 | 4/1993 | Minaskanian et al. | 514/182 |
| 5,208,225 | 5/1993 | Boissonneault et al. | 514/178 |
| 5,211,952 | 5/1993 | Spicer et al. | 424/426 |
| 5,214,030 | 5/1993 | Stief | 514/12 |
| 5,223,261 | 6/1993 | Nelson et al. | 424/443 |
| 5,232,703 | 8/1993 | Blank | 424/449 |
| 5,242,951 | 9/1993 | Akemi et al. | 514/772.5 |
| 5,248,676 | 9/1993 | Nakagawa et al. | 514/182 |
| 5,256,421 | 10/1993 | Casper | 424/449 |
| 5,256,652 | 10/1993 | El-Rashidy | 514/58 |
| 5,266,596 | 11/1993 | Yokokawa et al. | 514/567 |
| 5,276,022 | 1/1994 | Casper | 514/170 |
| 5,279,543 | 1/1994 | Glikfeld et al. | 604/20 |
| 5,288,717 | 2/1994 | Raveendranath et al. | 514/179 |
| 5,296,230 | 3/1994 | Chien et al. | 424/448 |
| 5,301,688 | 4/1994 | Stephen et al. | 607/99 |
| 5,314,694 | 5/1994 | Gale et al. | 424/448 |
| 5,314,906 | 5/1994 | Bombardelli | 514/411 |
| 5,320,597 | 6/1994 | Sage, Jr. et al. | 604/20 |
| 5,323,769 | 6/1994 | Bommannan et al. | 601/2 |
| 5,340,585 | 8/1994 | Pike et al. | 424/426 |
| 5,340,586 | 8/1994 | Pike et al. | 424/426 |
| 5,362,497 | 11/1994 | Yamada et al. | 424/449 |
| 5,439,938 | 8/1995 | Solomon et al. | 514/565 | ns/INCONTINENCE TREATMENT

TECHNICAL FIELD

The present invention relates to the delivery of an agent, and more particularly to intraurethral delivery of an agent for treating incontinence.

BACKGROUND

Urinary incontinence is an involuntary discharge of urine from the bladder. Incontinence can be caused by a variety of factors including pregnancy, estrogen deficiency, general weakening of the sphincter or pelvic floor muscles, surgery along the urinary tract, infection, and other maladies localized in the urinary tract. This condition is widespread and affects millions of people.

There are several types of incontinence including stress incontinence, urge incontinence, and total incontinence. Stress incontinence occurs when a person's body is under physical stress. People suffering from this type of incontinence might experience urine discharge during physically stressful events. Examples of stressful events include coughing, laughing, and rigorous exercise. Urge incontinence is characterized as an urgent desire to urinate and results in total discharge of the bladder. This type of incontinence can occur at any time, but frequently occurs when a person has a sudden change in their physical position. Total incontinence is characterized by a total lack of control over urine discharge and is frequently caused by a complete failure of the sphincter muscles.

Current treatments for incontinence vary widely. Many people have to wear protective underwear such as diapers or a urinary catheter that collects discharged urine. These types of control can be uncomfortable, unsightly, and socially awkward. Pelvic exercises are also used to strengthen weak pelvic muscles. However, such exercises have limited affect, especially if the person does not perform the exercises properly or on a regular basis. Additionally, surgery is often performed to tighten the sphincter muscles. Surgery is a rather severe treatment and is typically performed as a last resort if all other treatments fail.

Drug therapy is another alternative treatment for incontinence. The type of drug that is used can vary depending on the type and cause of incontinence. For example, menopausal and post-menopausal women often experience estrogen deficiency, which causes a variety of symptoms including a thinning of the urethral and vaginal mucosa. Thinning of the urethral mucosa can result in a lack of urethral pressure and thus stress incontinence. Estrogen replacement therapy may help to control menopause related incontinence because some of the estrogen will reach and stimulate the estrogen receptors in the urethral wall. The stimulation will trigger an increase in the thickness of the urethral mucosa, which increases urethral pressure and helps to control incontinence.

In practice, estrogen is administered vaginally, orally, or transdermally. These forms of administration can cause serious side effects because the estrogen is exposed to normal and healthy tissue outside the urinary tract, which is the desired treatment area. Examples of possible side effects include breast tenderness, vaginal bleeding, cancer such as endometrial carcinoma, susceptibility to hypertension, and risk of abnormal blood clotting. The risk of side effects is even greater if there is sustained use of estrogen over a prolonged period. Therefore, estrogen replacement therapy may carry too much risk if the only or main goal of the therapy is to treat incontinence.

Another problem with estrogen replacement therapy is that tissue other than the urethral wall will absorb a significant portion of the dose. Thus, a larger dose must be administered in order to get an effective amount of estrogen to the urinary tract. The difficulty is that use of a larger dose of estrogen increases the risk of side effects and also causes an increase in the amount of waste because tissue outside the target area will absorb a larger amount of estrogen.

Other agents that increase the tone of the internal and external sphincter muscles may be used to treat incontinence. Examples of these agents include sympathomimetics such as α-adrenergic agonists and nicotinic cholinergic agonists. However, current methods of delivering these agents have problems similar to the method for delivering estrogens. That is, areas outside the urinary tract are exposed to the agent, which increases the risk of side effects. For example, sympathomimetics can result in elevated blood pressure, stimulation of the central nervous system resulting in insomnia and anxiety, dizziness, tremors, and cardiac arrhythmias. Nicotinic cholinergic agonists can also have harmful effects because there are nicotinic cholinergic receptors in the skeletal muscles, autonomic ganglia, and the adrenal medulla. Thus, treatment using nicotinic cholinergic agonists also can cause a variety of side effects.

Incontinence and current methods for treating incontinence can have a very harmful effect on a person's social, psychological, and physical well being. The involuntary discharge of urine in a public place is embarrassing if the person is not wearing any type of protective underwear or a collection catheter. It can also cause great discomfort. As a result, many people might limit their social interaction outside the privacy of their home. Even if people do wear protective underwear or a catheter, they often cause unsightly and telling bulges in the clothing. Other forms of control also have limitations. For example, many people do not perform pelvic exercises properly or on a regular basis, which limits the exercise's effectiveness. Additionally, surgery can be dangerous and is only performed as a last result.

Regarding the use of agents for treating incontinence, current delivery techniques expose the agent to tissue outside of the desired treatment area, which is an inefficient use of the agent and dramatically increases the risk of side effects. Therefore, there is a need in the art for a method of delivering an agent that can treat incontinence with a reduced risk of side effects.

SUMMARY

The present invention is a method for treating incontinence in a patient that has a bladder and a urethra. The urethra forms a lumen for draining the bladder. The method includes the steps of delivering an agent into the lumen and passing the agent from the lumen to internal body tissue. The agent increases restriction of the lumen, thereby providing increased control over urine flow from the bladder.

DETAILED DESCRIPTION OF THE DRAWINGS

Illustrated embodiments of the devices used to perform the present invention will be described in detail with reference to the drawings, where like reference numerals represent the like parts and assemblies throughout several views.

DETAILED DESCRIPTION

Figure 1:
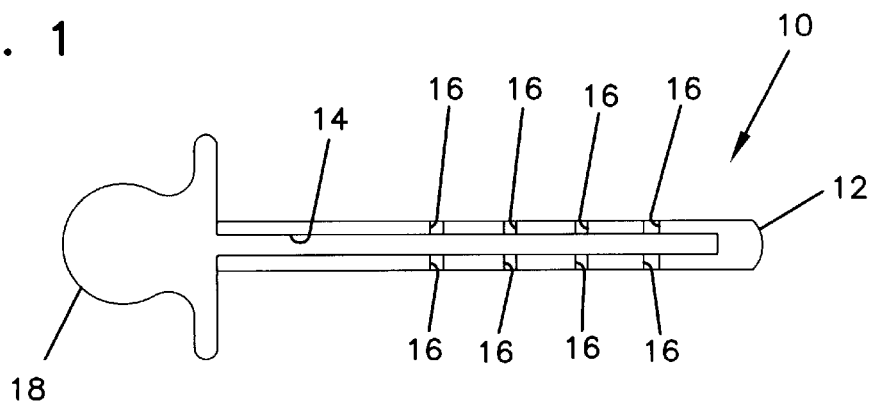
FIG. 1 shows a delivery device useful with the present invention, the delivery device having a suction bulb for storing and discharging an agent.

The invention initially will be described in general terms. The preferred embodiment of the invention will then be described in detail with reference to the drawings. Reference to the preferred embodiment does not limit the scope of the invention, which is limited only by the scope of the claims.

The present invention relates generally to direct intraurethral delivery of therapeutic agents that are effective for treating incontinence. Delivering a therapeutic agent directly through the urethra has several significant advantages. One advantage is that the agent is delivered directly to the receptors in the wall of the urethra and to the sphincter muscles. As a result, exposure of the agent to the reproductive organs as well as other parts of the body is diminished, which reduces the risk of side effects.

Minimizing the amount of agent that is delivered outside of the urinary tract also reduces waste. Thus, a smaller dose of the agent can be used with the present invention while increasing its effectiveness. In other words, the agent that is delivered into the patent will be used much more efficiently.

According to the present invention, the agent is delivered directly into the urethral lumen. The agent is then passed from the lumen into the wall of the urethra where it will cause an increase in urethral pressure. The agent accomplishes increased urethral pressure by one or more of the following: stimulating the estrogen receptors, α-adrenergic receptors, nicotinic cholinergic receptors, or other urethral mechanism.

The agent can be contained in many different forms. For example, the agent can be delivered as a liquid, cream, solution, emollient, gel, or spray. Additionally, the therapeutic agent can be delivered in microparticles composed of various biocompatible, biodegradable polymers. Examples of these types of polymers include polyester, polyalkylcyanoacrylate, polyorthoester, polyanhydride, albumin, gelatin, and starch. An advantages of microparticles is that they provide controlled and sustained release of the agent thereby minimizing the required dosing frequency.

The type of agent that can be delivered depends on the desired results. For example, estrogens may increase urethral pressure by increasing the thickness of the urethral mucosa. Moreover, estrogens may increase the number of adrenergic receptors on urethral smooth muscle. The estrogen can have several different forms including natural, synthetic, or semi-synthetic compounds. Examples of estrogens include estradiol, diethyl stilbestrol, estrone, estrone sodium sulfate, sodium equilin sulfate, ethinyl estradiol, quinestrol, diethylstilbestriol, mestranol, estriol, and chlorotrianisene. Although certain estrogens are set forth as an example, one skilled in the art will appreciate that other molecules will stimulate estrogen receptors and cause an increase in the thickness of the urethral mucosa.

Sympathomimetic agents generate urethral pressure by increasing the tone of the internal sphincter. The sympathomimetic agent will stimulate the α-adrenergic receptors in the internal sphincter, which will increase its tone. The internal sphincter will then tighten around the urethra and the neck of the bladder.

α-Adrenergic agonists are one type of sympathomimetic agent that can be effective. Various types of α-adrenergic agents include phenylephrine HCl, pseudoephedrine HCl, phenylpropanolamine HCl, ephedrine sulfate, norephedrine HCl, xylometazoline HCl, oxymetazoline HCl, naphazoline HCl, norepinephrine HCl, and privine HCl. Examples of other sympathomimetic agents include norepinephrine uptake inhibitors such as desipramine HCl, amitriptyline HCl, desmethylimipramine HCl, and imipramine HCl. Yet another sympathomimetic agent includes norepinephrine releasing agents such as tyramine. Although certain sympathomimetic agents are set forth as examples, one skilled in the art will appreciate that other agents will increase muscle tone of the internal sphincter and cause it to tighten around the urethra and the neck of the bladder. Although certain salts are specifically listed, one skilled in the art will further appreciate that other salts of the active ingredients can also be used.

Nicotinic cholinergic agonists and acetylcholinesterase inhibitors increase the tone of the external sphincter. Additionally, either of these types of agents can be combined with muscarinic cholinergic antagonist such as atropine, scopolamine, or glycopyrrolate. In this type of treatment, the agent will stimulate the nicotinic cholinergic receptors in the external sphincter, which will increase its tone and cause it to tighten around the urethra. Examples of nicotinic cholinergic agonists include choline, acetylcholine, methacholine, carbachol, bethanechol, arecoline, and *1,1-dimethyl-4-phenylpiperazinium iodide. Examples of acetylcholinesterase inhibitors include physostigmine salicylate, neostigmine Br, ambenomium Cl, edrophonium Cl, demecarium Br, and pyridostigmine Br. Although certain nicotinic cholinergic agonists, acetylcholesterases, and muscarinic cholinergic antagonists are set forth as examples, one skilled in the art will appreciate that other agents will cause the external sphincter muscle to increase its tone and tighten around the urethra. Although certain salts are listed, one skilled in the art will further appreciate that other salts of the active ingredients can also be used.

Additionally, estrogens and sympathomimetics such as an α-adrenergic agonist can be used in combination. Current medical research indicates that estrogens may increase the number of α-adrenergic receptors in the internal sphincter. Thus, the α-adrenergic agonists will stimulate both the preexisting and newly developed α-adrenergic receptors. The increased number of α-adrenergic receptors will cause the sphincter muscles to respond more efficiently to the α-adrenergic agonists and have an even greater increase in tone.

It may also be possible to treat urinary incontinence by delivering an agent such as a therapeutic gene. A therapeutic gene can be contained in a plasmid DNA together with a promoter. Genes could be delivered directly into the urethral wall using any of the embodiments or delivery techniques described in this specification. Because plasmids are large, highly negatively charged, and need to gain access to the intracellular compartment to be effective, devices that use iontophoresis to actively deliver the agent are preferred. Genes that encode for estrogen receptors, adrenergic receptors, or products that stimulate the growth of urethral mucosa, smooth muscle, or extracellular matrix could all potentially be used to increase the thickness of the mucosal lining of the urethra, the tone of the internal sphincter muscle, or the tone of the external sphincter muscle.

Other agents can be used that will enhance penetration of the therapeutic agent through the urothelium lining of the urethra and into the tissue of the urethral wall. The penetration enhancer may be mixed with the primary therapeutic agent for delivery. Examples of penetration enhancers include
dodecyl 2-(N.N.-dimethylamino)propionate; 1,8-CN; 1-[2-(decylthio)ethyl]azacyclopentan-2-one; 1-dodecylazacycloheptan-2-one; oleic acid; dimethylsulfoxide; 1-menthol; and 1-lauryl-2-pyrrolidone. Two of those penetration enhancers, dodecyl 2-(N.N-diemethylamino)propionate and oleic acid, are ionic agents that are deliverable during iontophoresis. Although specific examples are provided, one skilled in the art will realize that there are other penetration enhancers that may be useful with the present invention.

Referring now to FIGS. 1–5, many different devices can be used with the present invention. The basic method can employ any of the devices shown in these figures in order to directly deliver the therapeutic agent into the urethral lumen and into the urethral wall. These devices can include either passive or active delivery mechanisms. Passive delivery mechanisms rely on principles such as diffusion and absorption. Examples of active delivery mechanisms include pressure, iontophoresis, electroporation, and phonophoresis.

Referring to FIG. 1, one possible delivery device 10 includes a hollow probe 12 that defines a chamber 14 and a plurality of perforations 16 that extend from the chamber 14 to the surface of the probe 12. The chamber 14 opens to the interior of the suction bulb 18. The suction bulb 18 is sized to prevent the probe 12 from being inserted too far into the urethra. In use, the person will dip the probe 12 into a reservoir of the therapeutic agent and draw a supply into the suction bulb 18. The probe 12 is then inserted into the urethra and the bulb 18 is compressed. Compressing the bulb 18 causes the therapeutic agent to discharge into the urethral lumen where it is absorbed into the urethral wall.

Figure 2:
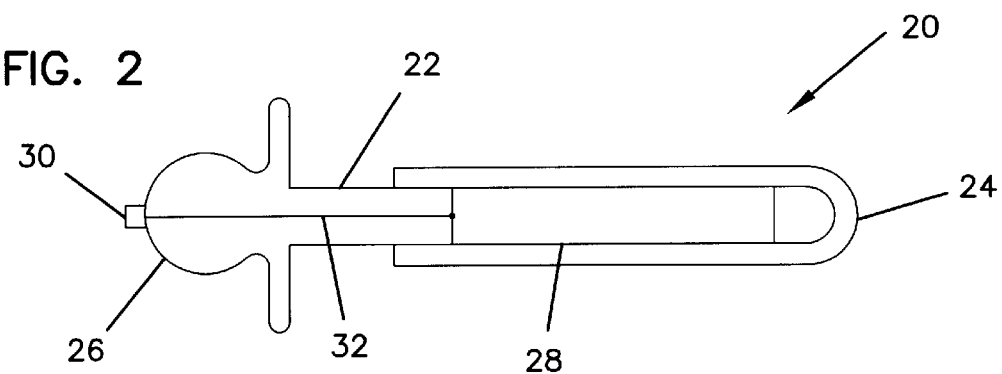
FIG. 2 shows a delivery device useful with the present invention, the delivery device having an absorbent sheath for retaining an agent and iontophoretic electrode.

Referring to FIG. 2, another possible delivery device 20 provides iontophoretic delivery of the therapeutic agent. This device 20 includes a probe 22 that is covered by a sheath 24 formed from a polymer matrix, an open-cell foam, or a hydrogel. An applicator handle 26 is mounted on the end of the probe 22 to provide easy handling and to prevent the probe 22 from being inserted too far into the urethra. An electrode 28 is mounted on the surface of the probe 22 and beneath the sheath 24. A connector 30 is mounted on the handle 26 and a lead 32 extends between the connector 30 and the electrode 28. Iontophoretic delivery of an agent is well known in the art.

In use, the sheath 24 is loaded with the therapeutic agent and the probe 22 is then inserted into the urethral lumen. The agent can be loaded by dipping the probe 22 into a reservoir of the agent. The patient can load the sheath themselves. If greater control of the dose is required, however, the patient can purchase sheaths from a pharmacist that has preloaded the agent.

After the probe 22 is inserted into the urethral lumen, the agent is passed into the urethral wall. This task is accomplished by placing a second electrode (not shown) on the patient's skin and passing an electric current between the electrode 28 and the second electrode. The electric current will either drive or drag the agent into the urethral wall.

Although the electrode 22 is described for use with iontophoresis, it could also be used for electroporation, which is well known in the art. Another embodiment might replace the electrode with an ultrasonic transducer (not shown) for phonophoretic delivery of the agent, which is also well known in the art.

If active delivery is not desired, the probe does not need to include the electrode 28. In this alternative embodiment, the sheath 24 could be mounted on a removable urethral insert (not shown) that is deposited in the urethra for sustained release of the therapeutic agent. The probe 22 would act as an insertion tool for the urethral insert. Alternatively, the probe 22 can be left inserted in the urethra until the agent is passively delivered from the sheath into the urethral wall.

Figure 3:
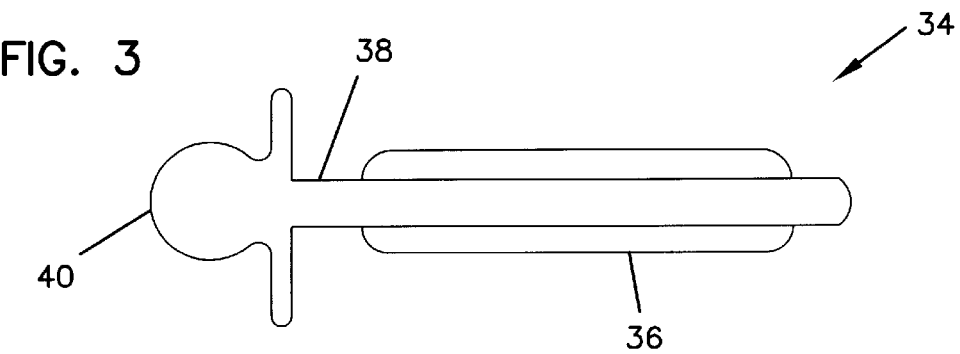
FIG. 3 shows a suppository and a tool useful with the present invention, the tool for inserting the suppository into the urethra.

Referring to FIG. 3, a device 34 for passive delivery includes a suppository 36 and an insertion tool 38. The insertion tool 38 has a handle 40 that provides easy handling and is sized to prevent the insertion tool 38 from being inserted too far into the urethra. The tool 38 is used to insert the suppository 36 into the urethral lumen. The suppository 36 will contain the agent, which will be absorbed in the urethral wall.

Figure 4:
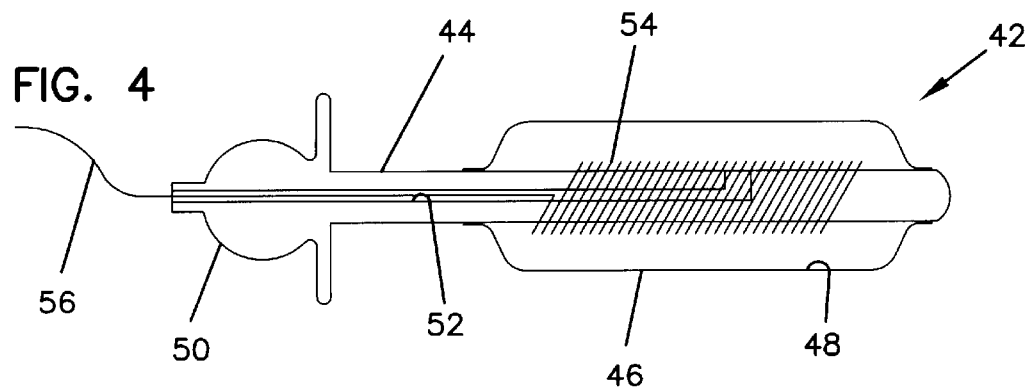
FIG. 4 shows a delivery device useful with the present invention, the delivery device having a porous balloon and a lumen for inflating the balloon with an agent.

Referring to FIG. 4, a delivery device 42 may include a probe 44 on which a porous balloon 46 is mounted. The balloon 46 defines a chamber 48. A handle 50 is attached to the probe 44 and is sized to prevent the probe 44 from being inserted too far into the urethra. The probe 44 defines a lumen 52 that extends from the handle 50 to the chamber 48 of the balloon 46. An electrode 54 is mounted on the probe 44 at a position within the chamber 48 of the balloon 46. A lead 56 is connected to the electrode 54 and extends through the lumen 52 for connection to a power supply (not shown). The electrode 54 could be replaced with an ultrasonic transducer (not shown) for phonophoretic delivery of the agent.

In use, the probe 44 is inserted into the urethral lumen. An agent is then injected into the chamber 48 via the lumen 52, which causes the balloon 46 to inflate and press against the urethral wall. Electric current is then caused to pass from the electrode 54 to another electrode (not shown) that is placed against the patient's skin. The current drives or drags the agent through the pores in the balloon 46 and into the urethral wall. Electroporation can also be used to enhance cellular uptake and penetration of the agent. The delivery device 42 can also be used without the electrode 54. In this alternative embodiment, the agent within the chamber is pressurized so that it will pass through the pores of the balloon 46 and be passively absorbed into the urethral wall.

Figure 5:
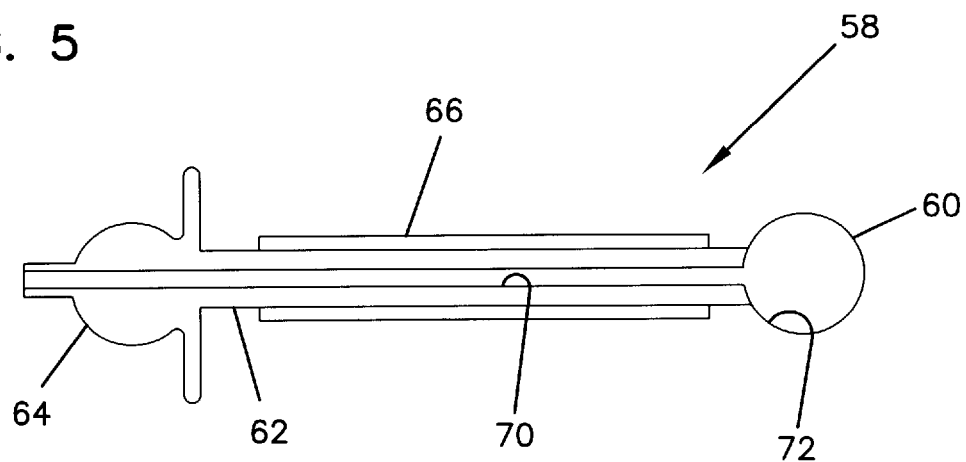
FIG. 5 shows a plug type delivery device useful with the present invention, the delivery device having a balloon for blocking the neck of the bladder and an absorbent sheath for retaining an agent.

Referring to FIG. 5, a delivery device 58 can include a balloon 60 for sealing the passage between the urethra and the bladder. This device is similar to the device shown in FIG. 2 and includes a probe 62, a handle 64 and a sheath 66, which is made from material such as a polymer matrix, an open-cell foam, or a hydrogel. The balloon 60 defines a chamber 72 and is mounted on the end of the probe 62 that is oppositely disposed from the handle 64. The balloon 60 is sized so that it fits through the neck of the bladder when deflated and blocks the passage between the bladder and urethra when inflated.

The probe 62 defines a lumen 70 that extends from the handle 64 to the chamber 72. An electrode (not shown) or an ultrasonic transducer (now shown) may be mounted on the probe 62.

The delivery device of FIG. 5 and associated delivery methods has several advantages. One advantage the device shown in FIG. 5 is that the balloon 60 can help to prevent the discharge of urine from the bladder before the effect of the therapeutic agent is realized. The therapeutic agents could cause the sphincter muscles to tighten around the probe 62 and reduce leakage even further. Thus, the delivery device could be left in the urethra for a period of time during sustained release of the therapeutic agent. If the probe 62 is left in the urethra for an extended period, the handle 64 can be much smaller and/or flatter for increased comfort and in order to prevent unsightly bulges.

Another advantage of the delivery device 58 is that the balloon 60 prevents the therapeutic agent from being delivered into the bladder and affecting the detrusor smooth muscle surrounding the bladder. Preventing this type of delivery is important because the detrusor smooth muscle contains muscarinic cholinergic receptors, which may be stimulated by some of the agents that may be used to increase the tone of the external sphincter muscle. Thus, these agents may cause contraction of the detrusor smooth muscle, thereby compressing the bladder and causing involuntary discharge of urine. Acetylcholine is an example of an agent that will stimulate the muscarinic cholinergic receptors.

If there is a risk that the agent might stimulate the muscarinic cholinergic receptors, an alternative to using the device shown in FIG. 5 is to use a precise form of delivery that will minimize the bladder's exposure to the agent. This type of delivery might utilize a cream, suppository, or iontophoresis. Another alternative is to mix the agent with a muscarinic antagonist, which will block the muscarinic cholinergic receptors to prevent stimulation by the agent. The muscarinic antagonist will not block the nicotinic cholinergic receptors and thus not prevent the agent from increasing the tone of the external sphincter muscle.

The devices described above are presented for purposes of example only and are not intended to limit the scope of the present invention. One skilled in the art will understand that there may be other devices capable of delivering the agent in and to the urethra and then passing the agent into the urethral wall.

It is anticipated that the agents, devices, and delivery method described above can be administered by the patient as needed. Some of the agents may provide significant improvements for long periods of time with a single application possibly up to 8–12 hours. Other agents may require delivery several times over the course of the day. Additionally, some agents might require application for an extended period before urethral pressure begins to significantly increase. Estrogen is an example of an agent that will require extended application before thickness of the urethral mucosa is developed and a significant benefit is realized.

Although the description of the preferred embodiments and methods have been quite specific, it is contemplated that various modifications could be made without deviating from the spirit of the present invention. Accordingly, it is intended that the scope of the present invention be dictated by the appended claims, rather than by the description of the preferred embodiments and methods.

The invention that we claim is:

1. A method of treating incontinence in a patient, the patient having a bladder and a urethra, the urethra forming a lumen for draining the bladder, the method comprising the steps of:

delivering an agent into the lumen, the agent being selected from the group consisting of estrogenic hormones, sympathomimetics, acetylcholinesterases, and cholinergic agonists; and passing the agent from the lumen to internal body tissue, the agent increasing restriction of the lumen thereby providing increased control over urine flow from the bladder.

2. The method of claim 1 wherein the internal body tissue includes estrogen receptors, further wherein the step of passing the agent from the lumen to internal body tissue comprises the step of stimulating the estrogen receptors thereby increasing thickness of a urethral mucosa.

3. The method of claim 1 wherein the step of delivering an agent comprises the step of delivering an estrogenic hormone.

4. The method of claim 3 wherein the step of delivering an estrogenic hormone comprises the step of delivering an estrogenic hormone selected from the group consisting of: estradiol, diethyl stilbesterol, estrone, sodium estrone sulfate, sodium equilin sulfate, ethinyl estradiol, quinestrol, diethylstilbestrol, mestranol, estriol, and chlorotrianisene.

5. The method of claim 1 wherein the step of delivering an agent comprises the step of delivering a sympathomimetic.

6. The method of claim 5 wherein the step of delivering a sympathomimetic comprises the step of delivering a norepinephrine uptake inhibitor selected from the group consisting of: desipramine, amitriptyline, desmethylimipramine, and imipramine.

7. The method of claim 5 wherein the step of delivering a sympathomimetic comprises the step of delivering a norepinephrine releasing agent.

8. The method of claim 1 wherein the internal body tissue comprises an external sphincter muscle and nicotinic cholinergic receptors, further wherein the step of passing the agent from the lumen to internal body tissue comprises the step of stimulating the nicotinic cholinergic receptors thereby increasing the tone of the external sphincter muscle.

9. The method of claim 8 wherein the step of delivering an agent comprises the step of delivering an acetylcholinesterase inhibitor.

10. The method of claim 9 wherein the step of delivering an acetylcholinesterase inhibitor comprises the step of delivering an acetylcholinesterase inhibitor selected from the group consisting of: physostigmine, neostigmine, ambenonium, edrophonium, demecarium, and pyridostigmine.

11. The method of claim 1 wherein the step of delivering an agent comprises the step of delivering a nicotinic cholinergic agonist.

12. The method of claim 11 wherein the step of delivering a nicotinic cholinergic agonist comprises the step of delivering a nicotinic cholinergic agonist selected from the group consisting of: choline, acetylcholine, methacholine, carbachol, bethanechol, arecoline, and *1,1-dimethyl-4-phenylpiperazinium iodide.

13. The method of claim 1 wherein the step of delivering an agent comprises delivering a cholinergic agonist, the method comprising the additional steps of:

delivering a muscarinic cholinergic antagonist into the lumen; and passing the muscarinic cholinergic antagonist from the lumen to internal body tissue.

14. The method of claim 1 comprising the additional steps of:

delivering a penetration enhancing agent into the lumen; and passing the penetration enhancing agent from the lumen to internal body tissue.

15. The method of claim 14 wherein the steps of delivering an agent and delivering a penetration enhancer into the lumen are performed simultaneously and the steps of passing the agent and passing the penetration enhancer are performed simultaneously.

16. The method of claim 15 wherein the step of delivering the penetration enhancer into the lumen comprises the step of selecting the penetration enhancer from the group consisting of: dodecyl 2-(N.N-diemethylamino)propionate, 1,8-CN; 1-azacyclopentan-2-one; 1-dodecylazacycloheptan-2-one; oleic acid; dimethylsulfoxide; 1-menthol; and 1-lauryl-2-pyrrolidone.

17. The method of claim 1 comprising the additional step of substantially sealing the opening from the lumen into the bladder before the step of delivering the agent into the lumen.

18. The method of claim 1 wherein the agent is in a fluid state and the step of passing the agent from the lumen to the internal body tissue comprises the steps of:

placing a first electrode in the lumen;

placing a second electrode in contact with the patient's body; and transmitting an electrical current between the first and second electrodes such that the electrical current passes from the lumen into the internal body tissue.

19. The method of claim 1 wherein the agent is in a fluid state and the step of passing the agent from the lumen to the internal body tissue comprises the steps of pressurizing the fluid within the lumen.

20. The method of claim 1 wherein the agent is in a fluid state and the step of passing the agent from the lumen to the internal body tissue comprises the steps of:

placing an ultrasonic transducer in the lumen; and emitting ultrasonic waves from the transducer such that the ultrasonic waves propagate into the internal body tissue.

21. The method of claim 1 wherein the agent is in a suppository and the step of delivering the agent into the lumen comprises the step of placing the suppository in the lumen.

22. The method of claim 1 wherein the urethra has a wall that defines the lumen and the agent is in a cream, further wherein the step of delivering the agent into the lumen comprises the step of applying the cream to the wall of the urethra.

23. The method of claim 1 wherein the step of delivering an agent into the lumen comprises spraying the agent into the lumen.

* * * * *